(12) United States Patent
Howald et al.

(10) Patent No.: US 8,632,601 B2
(45) Date of Patent: Jan. 21, 2014

(54) IMPLANT

(75) Inventors: Ralph Howald, Gossau (CH); Peter Heuberger, Raterschen (CH); Ulrike Trommsdorff, Zurich (CH)

(73) Assignee: Zimmer, GmbH, Winterthur (CH)

( * ) Notice: Subject to any disclaimer, the term of this patent is extended or adjusted under 35 U.S.C. 154(b) by 912 days.

(21) Appl. No.: 12/298,615

(22) PCT Filed: Apr. 24, 2007

(86) PCT No.: PCT/EP2007/053992
§ 371 (c)(1),
(2), (4) Date: Dec. 22, 2008

(87) PCT Pub. No.: WO2007/125060
PCT Pub. Date: Nov. 8, 2007

(65) Prior Publication Data
US 2009/0187252 A1   Jul. 23, 2009

(30) Foreign Application Priority Data

Apr. 28, 2006  (CH) ..................................... 0702/06

(51) Int. Cl.
*A61F 2/32* (2006.01)
(52) U.S. Cl.
USPC ..................................... 623/22.14; 623/22.11
(58) Field of Classification Search
USPC ................ 623/20.14–20.17, 20.21, 22.11, 623/22.14–22.16, 36, 56; 606/88, 89
See application file for complete search history.

(56) References Cited

U.S. PATENT DOCUMENTS

| | | | |
|---|---|---|---|
| 1,448,111 | A | 3/1923 | Eppler |
| 4,312,079 | A | 1/1982 | Dorre et al. |
| 4,355,429 | A | 10/1982 | Mittelmeier et al. |
| 4,467,479 | A | 8/1984 | Brody |
| 4,502,161 | A | 3/1985 | Wall |
| 4,769,039 | A | 9/1988 | Horber |
| 4,839,215 | A | 6/1989 | Starling et al. |
| 4,896,663 | A | 1/1990 | Vandewalls |
| 4,932,969 | A | 6/1990 | Frey et al. |

(Continued)

FOREIGN PATENT DOCUMENTS

| | | |
|---|---|---|
| DE | 1164019 B1 | 2/1964 |
| DE | 2015324 A1 | 11/1971 |

(Continued)

OTHER PUBLICATIONS

International Preliminary Report on Patentability mailed Feb. 11, 2010 in International Application No. PCT/US2008/071141.

(Continued)

*Primary Examiner* — Thomas J Sweet
*Assistant Examiner* — Christopher D Prone
(74) *Attorney, Agent, or Firm* — Schwegman, Lundberg, Woessner, P.A.

(57) ABSTRACT

The invention relates to an implant for relieving damaged areas of the surfaces of hip or shoulder joints from stress. Said implant can be introduced into the space between the joint surfaces of the condyle and the socket cooperating in the natural joint. The inventive implant is cup-shaped or cap-shaped, rests in the socket by a convex external face, and sits on the condyle by a concave internal face in the implanted state. The implant comprises at least two articulation layers which are movable relative to each other and encompass articulation surfaces that face one another in the implanted state.

20 Claims, 4 Drawing Sheets

(56) References Cited

U.S. PATENT DOCUMENTS

| | | | |
|---|---|---|---|
| 4,966,924 A | 10/1990 | Hyon et al. |
| 4,976,740 A | 12/1990 | Kleiner |
| 5,041,138 A | 8/1991 | Vacanti et al. |
| 5,080,678 A | 1/1992 | Spotomo et al. |
| 5,147,904 A | 9/1992 | Jocum et al. |
| 5,217,498 A | 6/1993 | Henssge et al. |
| 5,246,459 A | 9/1993 | Elias |
| 5,271,737 A | 12/1993 | Baldwin et al. |
| 5,282,861 A | 2/1994 | Kaplan |
| 5,312,409 A | 5/1994 | McLaughlin et al. |
| 5,314,478 A | 5/1994 | Oka et al. |
| 5,358,525 A | 10/1994 | Fox et al. |
| 5,370,700 A | 12/1994 | Sarkisian et al. |
| 5,458,643 A | 10/1995 | Oka et al. |
| 5,553,476 A | 9/1996 | Oehy et al. |
| 5,556,429 A | 9/1996 | Felt |
| 5,607,474 A | 3/1997 | Athanasiou et al. |
| 5,609,641 A | 3/1997 | Johnson et al. |
| 5,645,592 A | 7/1997 | Nicolais et al. |
| 5,658,343 A | 8/1997 | Hauselmann et al. |
| 5,795,353 A | 8/1998 | Felt |
| 5,817,098 A | 10/1998 | Albrektsson et al. |
| 5,871,541 A | 2/1999 | Gerber |
| 5,951,564 A | 9/1999 | Schroder et al. |
| 6,010,535 A * | 1/2000 | Shah ........................ 623/22.16 |
| 6,113,640 A | 9/2000 | Tormala et al. |
| 6,132,468 A | 10/2000 | Mansmann |
| 6,140,452 A | 10/2000 | Felt et al. |
| 6,168,630 B1 | 1/2001 | Keller et al. |
| 6,224,630 B1 | 5/2001 | Bao et al. |
| 6,231,605 B1 | 5/2001 | Ku |
| RE37,277 E | 7/2001 | Baldwin et al. |
| 6,306,177 B1 | 10/2001 | Felt et al. |
| 6,425,923 B1 | 7/2002 | Stalcup et al. |
| 6,443,988 B2 | 9/2002 | Felt et al. |
| 6,447,514 B1 | 9/2002 | Stalcup et al. |
| 6,494,917 B1 | 12/2002 | McKellop et al. |
| 6,530,956 B1 | 3/2003 | Mansmann |
| 6,533,818 B1 | 3/2003 | Weber et al. |
| 6,547,828 B2 | 4/2003 | Scott et al. |
| 6,620,196 B1 | 9/2003 | Treiu |
| 6,629,997 B2 | 10/2003 | Mansmann |
| 6,652,587 B2 | 11/2003 | Felt et al. |
| 6,652,588 B2 | 11/2003 | Hayes, Jr. et al. |
| 6,679,913 B2 | 1/2004 | Homsy |
| 6,719,797 B1 | 4/2004 | Ferree |
| 6,827,743 B2 | 12/2004 | Eisermann |
| 6,994,730 B2 | 2/2006 | Posner |
| 7,001,431 B2 | 2/2006 | Bao et al. |
| 7,077,865 B2 | 7/2006 | Bao et al. |
| 7,291,169 B2 | 11/2007 | Hodorek |
| 2001/0033857 A1 | 10/2001 | Vyakaman et al. |
| 2001/0039455 A1 | 11/2001 | Simon et al. |
| 2002/0022884 A1 | 2/2002 | Mansmann |
| 2002/0029083 A1 | 3/2002 | Zucherman et al. |
| 2002/0127264 A1 | 9/2002 | Felt et al. |
| 2002/0128715 A1 | 9/2002 | Bryan et al. |
| 2002/0156531 A1 | 10/2002 | Felt et al. |
| 2002/0161448 A1 | 10/2002 | Hayes, Jr. et al. |
| 2002/0173852 A1 | 11/2002 | Felt et al. |
| 2002/0173855 A1 | 11/2002 | Mansmann |
| 2002/0183845 A1 | 12/2002 | Mansmann |
| 2002/0183850 A1 | 12/2002 | Felt et al. |
| 2002/0188300 A1 | 12/2002 | Arramon et al. |
| 2002/0193883 A1 | 12/2002 | Wironen |
| 2003/0008396 A1 | 1/2003 | Ku |
| 2003/0074076 A1 | 4/2003 | Ferree et al. |
| 2003/0078617 A1 | 4/2003 | Schwartz et al. |
| 2003/0130741 A1 | 7/2003 | McMinn |
| 2003/0153918 A1 | 8/2003 | Putnam et al. |
| 2003/0163202 A1 | 8/2003 | Lakin |
| 2003/0195628 A1 | 10/2003 | Bae et al. |
| 2003/0220649 A1 | 11/2003 | Bao et al. |
| 2004/0010312 A1 | 1/2004 | Enayati |
| 2004/0039447 A1 | 2/2004 | Simon et al. |
| 2004/0051213 A1 | 3/2004 | Muratoglu |
| 2004/0107000 A1 | 6/2004 | Felt et al. |
| 2004/0133275 A1 | 7/2004 | Mansmann |
| 2004/0138754 A1 | 7/2004 | Lang et al. |
| 2004/0153163 A1 | 8/2004 | Posner |
| 2004/0163681 A1 | 8/2004 | Verhaverbeke |
| 2004/0199250 A1 | 10/2004 | Fell |
| 2004/0220582 A1 | 11/2004 | Keller |
| 2004/0236424 A1 | 11/2004 | Berez et al. |
| 2004/0247641 A1 | 12/2004 | Felt et al. |
| 2004/0267371 A1 | 12/2004 | Hayes, Jr. et al. |
| 2005/0021042 A1 | 1/2005 | Marnay et al. |
| 2005/0043808 A1 | 2/2005 | Felt et al. |
| 2005/0075642 A1 | 4/2005 | Felt et al. |
| 2005/0125077 A1 | 6/2005 | Harmon et al. |
| 2005/0171604 A1 | 8/2005 | Michalow |
| 2005/0251149 A1 | 11/2005 | Wenz |
| 2005/0251266 A1 | 11/2005 | Maspero et al. |
| 2005/0287187 A1 | 12/2005 | Mansmann |
| 2006/0009853 A1 | 1/2006 | Justin et al. |
| 2006/0079905 A1 | 4/2006 | Beyar et al. |
| 2006/0224244 A1 | 10/2006 | Thomas et al. |
| 2006/0235542 A1 | 10/2006 | Hodorek et al. |
| 2006/0253200 A1 | 11/2006 | Bao et al. |
| 2007/0027230 A1 | 2/2007 | Beyar et al. |
| 2007/0038300 A1 | 2/2007 | Bao et al. |
| 2007/0088444 A1 | 4/2007 | Hodorek |
| 2007/0142916 A1 | 6/2007 | Olson et al. |
| 2007/0179607 A1 | 8/2007 | Hodorek et al. |
| 2007/0224238 A1 | 9/2007 | Mansmann et al. |
| 2008/0051889 A1 | 2/2008 | Hodorek |
| 2008/0215057 A1 | 9/2008 | Willi |
| 2008/0221700 A1 | 9/2008 | Howald |

FOREIGN PATENT DOCUMENTS

| | | | |
|---|---|---|---|
| DE | 2501080 A1 | 7/1976 | |
| DE | 2933174 A1 | 4/1980 | |
| DE | 2953575 A1 | 7/1982 | |
| DE | 3923418 A1 | 1/1991 | |
| DE | 4317448 A1 | 11/1994 | |
| DE | 29513894 U1 | 11/1995 | |
| DE | 19721661 A1 | 11/1998 | |
| DE | 19803183 A1 | 8/1999 | |
| DE | 10021387 A1 | 11/2001 | |
| DE | 20303205 U1 | 4/2003 | |
| DE | 10220368 A1 | 12/2003 | |
| DE | 10339605 A1 * | 4/2005 | ................ A61F 2/30 |
| DE | 10339605 A1 | 4/2005 | |
| EP | 0013863 A1 | 8/1980 | |
| EP | 0013864 A1 | 8/1980 | |
| EP | 0017930 A1 | 10/1980 | |
| EP | 0170779 A1 | 2/1986 | |
| EP | 0528080 A1 | 2/1993 | |
| EP | 0480954 B1 | 4/1993 | |
| EP | 0552949 A1 | 7/1993 | |
| EP | 0577529 A1 | 1/1994 | |
| EP | 0639356 A1 | 2/1995 | |
| EP | 0768066 A2 | 4/1997 | |
| EP | 0892627 B1 | 1/1999 | |
| EP | 0992222 A2 | 4/2000 | |
| EP | 0507645 B1 | 7/2001 | |
| EP | 1340477 A2 | 9/2003 | |
| EP | 1407728 A1 | 4/2004 | |
| EP | 1477120 A1 | 11/2004 | |
| EP | 1588669 A1 | 10/2005 | |
| FR | 2519545 A1 | 7/1983 | |
| FR | 2691355 A1 | 11/1993 | |
| FR | 2692140 A1 | 12/1993 | |
| FR | 2803190 A1 | 7/2001 | |
| FR | 2803191 A1 | 7/2001 | |
| GB | 1126961 | 11/1968 | |
| GB | 1349987 A | 4/1974 | |
| GB | 2139097 A | 11/1984 | |
| WO | WO97/37613 A1 | 10/1997 | |
| WO | WO00/15153 A1 | 3/2000 | |
| WO | WO00/23009 A1 | 4/2000 | |
| WO | WO01/45595 A2 | 6/2001 | |
| WO | WO02/41808 A1 | 5/2002 | |

(56) References Cited

FOREIGN PATENT DOCUMENTS

| WO | WO02/054992 A | 7/2002 | |
| WO | WO2004/032987 A | 4/2004 | |
| WO | WO 2004032987 A1 * | 4/2004 | ............ A61L 27/44 |
| WO | WO2005/051242 A1 | 6/2005 | |
| WO | WO2006/060555 A1 | 6/2006 | |
| WO | WO2007/054553 A1 | 5/2007 | |
| WO | WO2007/090790 A2 | 11/2007 | |
| WO | WO2007/090790 A3 | 11/2007 | |
| WO | WO2007/125060 A1 | 11/2007 | |

OTHER PUBLICATIONS

Office Action mailed Oct. 28, 2010 in U.S. Appl. No. 12/179,707.
Office Action mailed Jul. 8, 2010 in U.S. Appl. No. 12/278,835.
Response filed Oct. 1, 2010 in U.S. Appl. No. 12/278,835.
International Preliminary Report on Patentability mailed Sep. 9, 2008 in International Application No. PCT/EP2007/051008.
Quinton, J.S. and P.C. Dastoor, "Characterizing the bonding mechanisms at silane-metal interfaces: a model system", J. Mat. Sci. Letters, vol. 18, Nov. 1999, pp. 1833-1835.

* cited by examiner

IMPLANT

This application is a U.S. National Phase Patent Application claiming priority to International Application Serial No. PCT/EP2007/053992 filed on Apr. 24, 2007, which claims priority to Swiss Application Serial No. CH 00702/06, filed on Apr. 28, 2006, the disclosures of which are hereby explicitly incorporated by reference herein in their entirety.

The invention relates to an implant for relieving damaged areas of the surfaces of hip or shoulder joints from stress. Said implant can be introduced into the space between the joint surfaces of the condyle and the socket cooperating in the natural joint. The inventive implant is cup-shaped or cap-shaped, rests in the socket by a convex external face, and sits on the condyle by a concave internal face in the implanted state. The implant comprises at least two articulation layers which are movable relative to each other and encompass articulation surfaces that face one another in the implanted state.

The invention is concerned with an implant for relieving of the injured areas of the articular surfaces of the hip joints or shoulder joints.

Generally in known joint prostheses both articular surfaces are replaced through artificial joint parts, which are coordinated with each other. This takes place, as it is known, within operations, in which depending on the prosthesis used a more or less large part of the healthy bones is removed. For example, in hip operations the femur head is completely or partially removed, in order to create space for an articular head, which in the majority of cases is anchored through a shaft in the femur. Accordingly during the operation bone material is removed through an appropriate procedure at the acetabulum (socket of the hip joint) of the hip bone, in order to be able to add an artificial joint socket or joint cup, which serves for the support of the artificial articular head.

Such operations involve not insubstantial exposures and risks for the patients. It presents a problem for relatively young patients that a flawless function of an artificial joint can not be guaranteed for arbitrarily long periods of time. In many cases repeated operations are required. However such interventions are frequently associated with difficulties, since already the first operation has cost the patient an often not insubstantial part of the healthy bone material.

The first operation, which leads to a relevant loss of bone material, can be postponed by the means of so-called resurfacing techniques. In this connection only surfaces of the affected joint are replaced through a comparatively thin, plate-shaped or cup-shaped implant. However also these known techniques require stressful operations, which are also not possible with minimal invasion. Furthermore also in the case of resurfacing it is required to remove healthy bone material in the area of the involved articular surfaces, but in a smaller amount than in the operations, mentioned before.

These considerations are of importance mainly in the cases, when the articular surfaces are affected by arthrosis and the involved bones themselves are intact, that is fractures should not be treated. Such joint injuries happen also to relatively young patients, for which reason a need for techniques for treatment of injured articular surfaces exists, in which the healthy bone material possibly stays preserved. In order to maintain the exposures for the patients as little as possible, such techniques should be conducted with minimal invasion.

The invention provides an implant for relieving of the injured areas of the articular surfaces, which can be inserted in the gap between articular surfaces of the articular head and the joint socket, which are interdependent in the natural joint, whereat the implant, in the implanted state, is bowl-shaped or plate-shaped, with a convex outer side it is situated in the joint socket and it sits on the articular head with a concave inner side, and whereat the implant includes at least two articulation panels, which are relatively movable to each other, with articular surfaces, which are facing each other, in the implanted state.

The implant can considerably reduce the exposures to pressure and/or shear pressures of the areas of the articular surfaces, affected by arthrosis. Thereby the implant is suited not exclusively, but very well for joints, affected by the arthrosis in an early stage.

The point of time, when the first operation, described in the beginning, becomes necessary, can be postponed through the implant. Therefore the implant is of special interest for relatively young patients.

It is an advantage that the implant can be inserted within minimal-invasive interventions. No conditioning of the bone is required. Though techniques for inserting the implant, in which bones and cartilage are conditioned are possible. But then such bone conditioning serves not primarily for adaptation or preparation of the articular surfaces or joint socket, but solely for insertion of the implant into the gap between the articular surfaces.

Implantation methods, in which bones and/or cartilage are conditioned or removed, are also conceivable and possible.

The implant facilitates the configuration, in which an articulation between articular head and joint socket occurs exclusively through articular surfaces of the implants and no articulation takes place between the implant and articular surfaces of the articular head and joint socket. In this connection the implant can be designed so that the articulation panels of the implant can be mechanically secured onto the articular surfaces of the articular head and joint socket by the means of the appropriate instruments. It is also possible to design at least the outer sides of the articulation panels of the implant, which face the articular surfaces, so that it will grow together with the articular surfaces.

The implant can be designed so that it aligns itself in the joint gap. Alternatively the implant can be secured to the natural bone structures or tissue structures.

Further it is an advantage that the insertion of the implant does not require subluxation of the articular head.

The implant can be produced from a flexible material, which is malleable for the insertion of the implant into the gap, existing between the articular surfaces. The plasticity of the implant allows implementation of different minimal-invasive operation techniques.

Furthermore, the implant can include a sealed structure, which surrounds the gap between the articulation panels. Through this the gap between the articulation panels is sealed hermetically from the surroundings. As an example, the implant can be designed as a closed bubble or balloon. Thereby it is possible that the implant includes a single closed material panel and the articulation panels are formed from sections of the single material panel, which face each other, in the implanted state. It is alternatively possible that the implant includes a multitude of individual material panels, from which at least two adjoining material panels form the articulation panels. In this connection the articulation panels can be connected to each other by their edges. The connection of the articulation panels can be formed as a sealing gasket, which seals the gap between the articulation panels from the surrounding area.

A closed implant has the advantage that all articulation movements take place within the implant and material abrasion, which potentially occurs due to the interaction of the articulation panels, stays within the implant.

However it is not mandatory to design the implant closed. Also an open implant can be utilized. The implant as an example can be open on the borders of the articulation panels.

It has been shown that through an appropriate material and/or through an appropriate material coating for the implant the natural joint function can be maintained.

The articular surfaces can be provided with a coating, which inhibits deterioration and/or formation of abrasion. The appropriate coatings can be provided also on the outer sides of the articulation panels.

The implant can be produced from one or several different metallic or non-metallic materials. For example a hydrogel, polyurethane or polyethylene are considered.

The implant can contain a textile material or consist of a textile material, whereat the textile material includes a textile substrate, and whereat a coating is provided at least on one part of the surface of the textile substrate, which contains a compound of two or more compounds in any combination, selected from the following group of compounds: hydrogel, polyurethane, polyvinyl chloride and polytetrafluoroethylene.

The textile substrate can consist of fibers, whereat at least one part of the fibers is provided with a coating, which contains a compound of two or more compounds in any combination, selected from the following group of compounds: hydrogel, polyurethane, polyvinyl chloride and polytetrafluoroethylene.

Herewith antifriction characteristics can be realized, which match the natural conditions in the joint to a large extent.

The implant or at least an articulation panel can be provided with a strengthening element, made from textile, fiber, weaving, textile fabric or webbing.

A method for insertion of an implant, which serves for relieving of the injured areas of the articular surfaces of the hip joints or shoulder joints, in the gap between articular surfaces of the articular head and the joint socket that are interdependent in the natural joint, can include, pursuant to an execution example, the following: designing a channel in the articular head or the joint socket, which flows into the gap between articular surfaces, inserting the implant into the channel, and inserting the displacement medium into the channel, in order to push the implant through the channel into the gap.

In hip operations the channel can be designed, beginning in the area of the greater trochanter, and then going through the femoral neck and the femoral head.

Further possible execution examples result from the contingent claims, the description, as well as figures.

The invention is described in the following with references to the figures.

The implant can be inserted for both: hip joint and shoulder joint. Below further execution examples will be explained, namely in the connection to the hip joint.

Regarding the materials, used for the implant, and the possible coatings, as well as further possible designs, it is referred to the introduction part.

Figure 1:
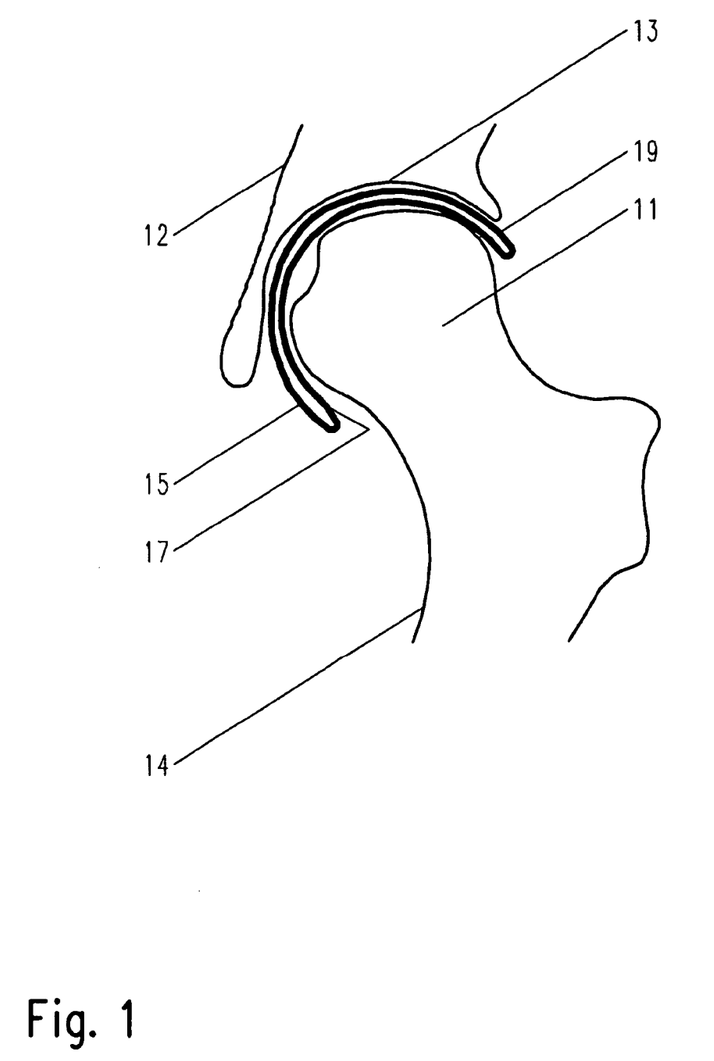
FIGS. 1 and 2 show an execution example of an implant, pursuant to the invention.
Figure 2:
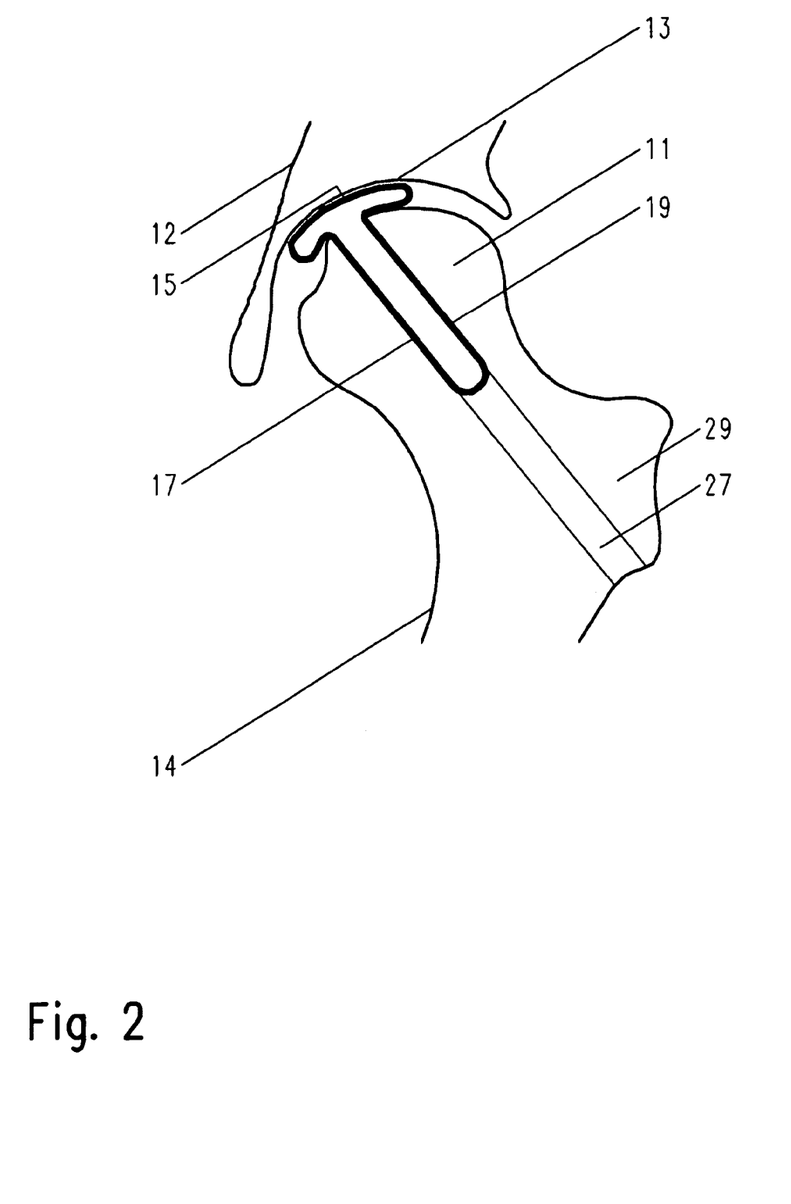

The implant, pursuant to FIGS. 1 and 2, includes a single closed material panel 19. In the implanted state, pursuant to FIG. 1, the implant, designed as a closed bubble or balloon, is located in the gap between the articular surfaces of the femur head 11 and the joint socket 13. In this state two sections of the material panel 19, which forms in a way a "balloon", are located directly on top of each other. In the following these sections are referred to as articulations panels 15, 17, since the inner surfaces of the articulations panels 15, 17, facing each other, touch each other and therefore they work as articular surfaces of the joint for the movements of the joint.

The inner side of the implant and therewith the articular surfaces can be coated with a wear resistant material. Alternatively or additionally an anti-friction coating or lubricant is used, which is applied to the inner side of the implant before production of the closed structure, for example in form of a fluid.

An advantage of a closed structure of the implant is that the abrasion, which possibly occurs due to the movements of the articular surfaces against each other, remains inside of the implant and cannot enter the body of the patient.

Furthermore, the implant can be created so that between its outer sides and the articular surfaces of the joint socket 13 and articular head 11 no relative movements (or at least present not to the relevant extent) take place, so that during joint movements the articulation occurs practically exclusively between articular surfaces of the articulation panels 15, 17, facing each other, and therewith exclusively inside of the closed implant.

For this the implant can be mechanically secured with its outer sides to the hip bones 12 and to the femur 14, using the appropriate instruments. Alternatively or additionally such implant material can be found, that it will grow together with the articular surfaces of the joint socket 13 and articular head 11 on its outer side or will build a strong connection to the articular surfaces another way.

The insertion of the implant can take place within an arthroscopic surgery. For example, the articular surfaces can be separated by the means of an extraction table, namely without subluxation of the femur head 11.

The insertion of the implant can also occur using other minimal-invasive techniques.

A possible insertion of the implant is presented in FIG. 2. Starting from a point in the area of the greater trochanter 29 a channel 27 is drilled in the bones, which runs through the femoral neck and the femoral head 11 and ends in the gap between the articular surfaces. Subsequently the implant is inserted into the channel 27. The implant is pushed through the channel 27 into the gap between the articular surfaces by the use of fluid that is under pressure, which is brought into the channel 27.

Figure 3:
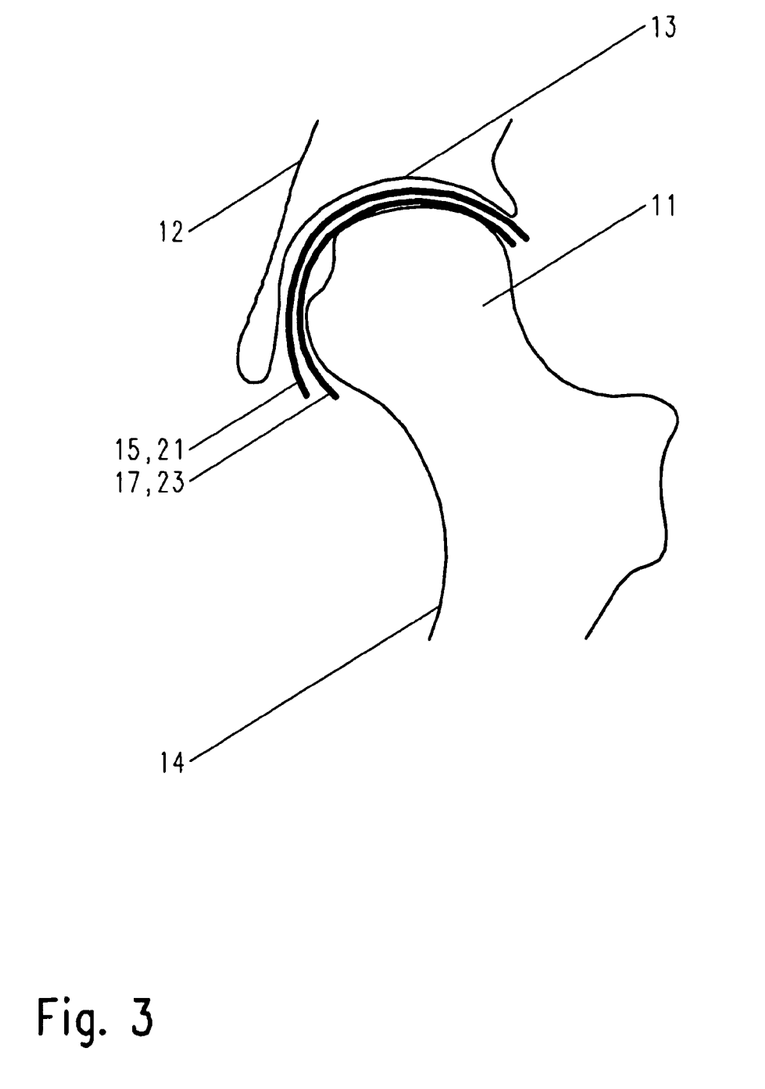
FIG. 3 shows another execution example, pursuant to the invention.

Another execution example of an implant is shown in FIG. 3. The implant includes two individual material panels 21, 23, which form articulation panels 15, 17 with articular surfaces, facing each other. In contrast to the closed version, shown in FIGS. 1 and 2, the implant in the implanted state, in accordance with FIG. 3, is open at the edges of the bowl-shaped or plate-shaped articulation panels 15, 17.

Figure 4:
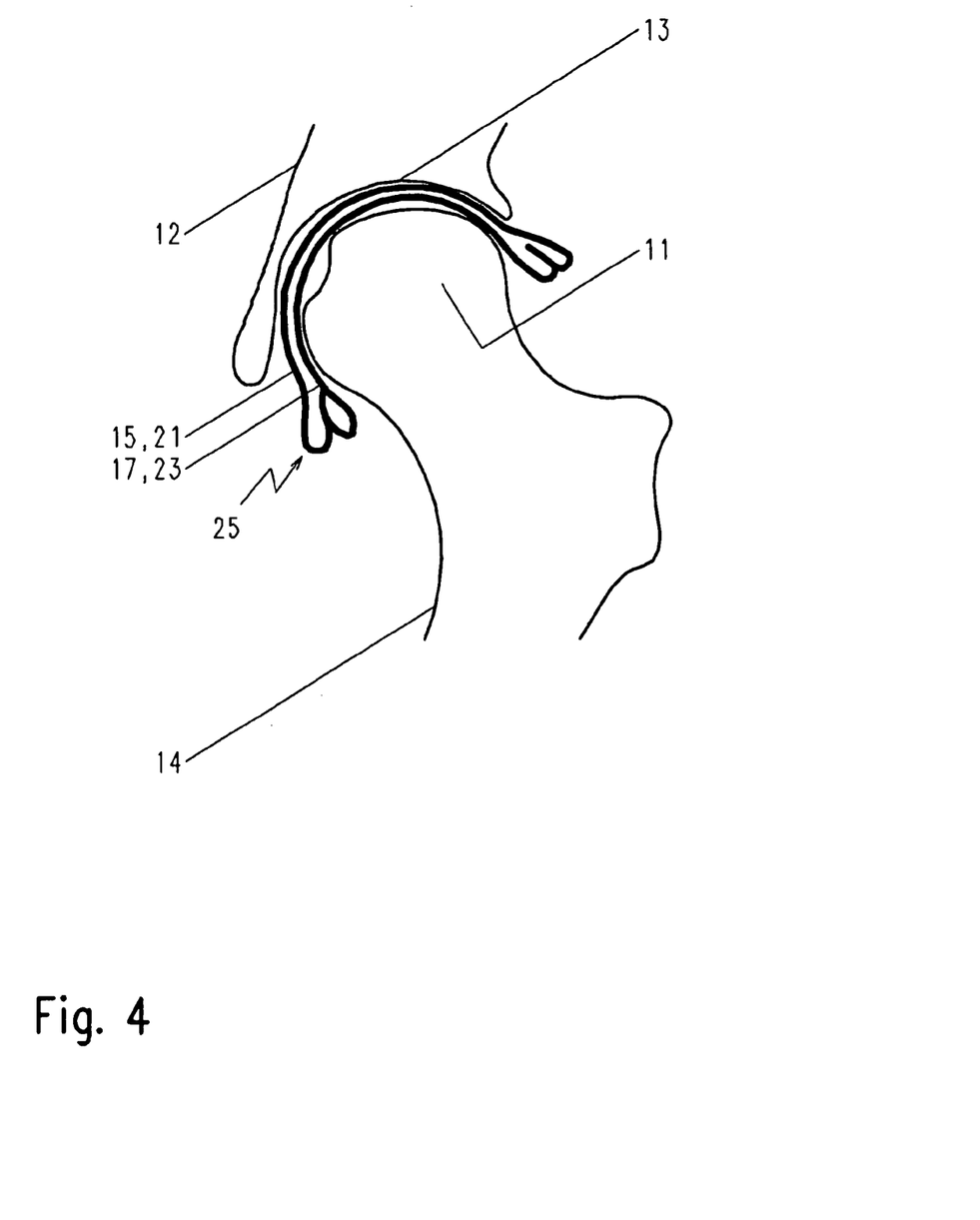
FIG. 4 shows another execution example, pursuant to the invention.

FIG. 4 shows an execution example, which is based on the execution example of FIG. 3. In contrast to the open structure, in accordance with FIG. 3, both individual material panels 21, 23 are connected to each other by their edges. The connection forms a material section, which works as a sealing gasket 25, which seals a gap between both articulation panels 15, 17 from the surroundings and therewith closes the implant.

The sealing of the sealing gasket 25 takes place through the fluid pressure, which is prevalent inside of the implant.

Similar to the execution examples of FIGS. 1 and 2, advantages of the configuration, in accordance with FIG. 4, are not only that material abrasion which possibly develops, stays inside of the implant, but also beyond it, the sealing gasket 25 facilitates a larger moving area, compared to the case of the execution example of FIGS. 1 and 2.

List of Figure References 11 articular head
12 hip bones
13 joint socket
14 femur
15 articulation panel
17 articulation panel
19 material panel
21 material panel
23 material panel
25 sealing gasket
27 channel
29 greater trochanter

The invention claimed is:

1. A method for enhancing articulation between a first joint surface and a second joint surface with a prosthetic device, said first joint surface and said second joint surface forming a joint, said prosthetic device including a first panel and a second panel, said first panel and said second panel being deformable and having articulation surfaces, said articulation surfaces of said first panel and of said second panel facing each other in an implanted state, said first panel being sized and shaped to be positioned over at least a portion of the first joint surface, and said second panel being sized and shaped to be positioned over at least a portion of the second joint surface; said method comprising:

creating a channel in a bone, said bone comprising the second joint surface and said channel having a first aperture in fluid communication with a second aperture which is positioned in said second joint surface of said bone, a cross-sectional area of said channel being smaller than said first panel and said second panel in said implanted state;

inserting into said channel through said first aperture, in order, a first panel central portion of said first panel, a first peripheral region of said first panel which extends from said first panel central portion, and said second panel;

applying pressure to said prosthetic device to move said prosthetic device through said channel until said first panel central portion, said first peripheral region and said second panel emerge through said second aperture, said first panel central portion emerging first and being pressured against said first joint surface, said first peripheral region emerging after said first panel central portion, said pressure causing said first peripheral region to unfurl away from said second aperture as said second panel emerges through said second aperture.

2. The method of claim 1, wherein the applying step comprises applying pressure with a displacement medium against said second panel.

3. The method of claim 2, wherein said displacement medium comprises a fluid.

4. The method of claim 1, wherein said joint comprises a joint head and a joint socket, and wherein said second aperture is positioned in one of said joint head and said joint socket.

5. The method of claim 4, further including separating the first and second joint surfaces without subluxation of the joint head from the joint socket.

6. The method of claim 4, wherein said joint socket comprises an acetabulum.

7. The method of claim 1, wherein said bone comprises a femur, said first aperture is positioned in a greater trochanter of said femur, and said second aperture is positioned in a femoral head of said femur.

8. The method of claim 1, further including the step of extracting said prosthetic device from said channel.

9. The method of claim 1, wherein the applying step includes positioning said prosthetic device between the first and second joint surfaces.

10. The method of claim 1, further including the step of mechanically securing said device to at least one of said first joint surface and second joint surface.

11. The method of claim 1, wherein said first panel comprises a securement surface opposite said articulation surface, and wherein said securement surface is configured to promote growth of cells forming said first joint surface onto said securement surface thereby securing said device to said first joint surface.

12. The method of claim 1, wherein said first peripheral region is connected to said second panel.

13. The method of claim 12, wherein said first peripheral region and a second peripheral region of said second component which extends from a central region of said second panel form a seal.

14. The method of claim 13, wherein said first panel and said second panel form an internal region, said first peripheral region is folded over, said second peripheral region is folded over and faces said first peripheral region, said first peripheral region and said second peripheral region defining a folded portion of said implant, and said seal is formed by a fluid pressure created by a fluid located in said internal region against said folded portion.

15. An implant for enhancing articulation between a first joint surface and a second joint surface, said first joint surface and said second joint surface forming a joint, said implant comprising:

a first component being deformable and having a first panel, said first panel having an articulation surface opposite an external surface and being sized and shaped to be positioned over at least a portion of the first joint surface, a peripheral region of said first component being folded over and defining a first inverted portion; and a second component being deformable and having a second panel, said second panel having an articulation surface opposite an external surface and being sized and shaped to be positioned over at least a portion of the second joint surface, a peripheral region of said second component being folded over and defining a second inverted portion, wherein said articulation surface of said first panel and said articulation surface of said second panel face each other and are movable relative to each other in the implanted state, and wherein said first inverted portion of said first component faces said second inverted portion of said second component defining a folded portion of said implant.

16. The implant of claim 15, wherein said folded portion of said implant forms a seal when a fluid located in said implant applies fluid pressure against said first inverted portion and said second inverted portion of said first and said second components.

17. The implant of claim 15, wherein said articulation surfaces are coated with an abrasion resistive material.

18. The implant of claim 17, wherein said abrasion resistive material is selected from the group consisting of hydrogel, polyurethane, polyvinyl chloride and polytetrafluoroethylene.

19. The implant of claim 15, wherein at least one of said first component and said second component comprises a fibrous material.

20. The implant of claim 15, wherein at least one of said first component and said second component comprises two or more panels.

* * * * *

UNITED STATES PATENT AND TRADEMARK OFFICE
CERTIFICATE OF CORRECTION

| | | |
|---|---|---|
| PATENT NO. | : 8,632,601 B2 | Page 1 of 1 |
| APPLICATION NO. | : 12/298615 | |
| DATED | : January 21, 2014 | |
| INVENTOR(S) | : Howald et al. | |

It is certified that error appears in the above-identified patent and that said Letters Patent is hereby corrected as shown below:

In the Claims

In column 5, line 43, in Claim 1, after "panel;", insert --and--, therefor

Signed and Sealed this
Seventeenth Day of March, 2015

Michelle K. Lee
*Director of the United States Patent and Trademark Office*

UNITED STATES PATENT AND TRADEMARK OFFICE
CERTIFICATE OF CORRECTION

PATENT NO. : 8,632,601 B2  Page 1 of 1
APPLICATION NO. : 12/298615
DATED : January 21, 2014
INVENTOR(S) : Howald et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1088 days.

Signed and Sealed this
Twenty-second Day of September, 2015

Michelle K. Lee
*Director of the United States Patent and Trademark Office*